US005753510A

United States Patent [19]

Kraus

[11] Patent Number: 5,753,510
[45] Date of Patent: May 19, 1998

[54] CALIBRATOR FOR USE IN TEST METHODS FOR DETECTING A DEFECTIVE COAGULATION FACTOR V

[75] Inventor: Michael Kraus, Marburg, Germany

[73] Assignee: Behring Diagnostics GmbH, Marburg, Germany

[21] Appl. No.: 551,838

[22] Filed: Nov. 7, 1995

[30] Foreign Application Priority Data

Nov. 9, 1994 [DE] Germany ............... 44 39 756.9

[51] Int. Cl.$^6$ ............... C12Q 1/56; G01N 33/86; G01N 33/96
[52] U.S. Cl. ............... 436/16; 436/8; 436/15; 436/17; 436/69
[58] Field of Search ............... 436/8, 15, 16, 436/35, 69, 17

[56] References Cited

U.S. PATENT DOCUMENTS

| | | | |
|---|---|---|---|
| 5,221,614 | 6/1993 | Enomoto | 435/13 |
| 5,387,503 | 2/1995 | Selmer et al. | 435/5 |

FOREIGN PATENT DOCUMENTS

WO 94/17415  8/1994  WIPO.

OTHER PUBLICATIONS

Esmon, "Protein S and Protein C Biochemistry, Physiology, and Clinical Manifestation of Deficiencies", Trends Cardiovasc Med., 2(6):214–219 (1992).

Rick, et al., "Factor IXa and von Willebrand factor modify the inactivation of factor VII by activated protein C", J. Lab Clin Med., 115(4):415–421 (1990).

Amer, et al., "Impairment Of the Protein C Anticoaqulant Pathway In A Patient With Systemic Lupus Erthematosus, Anticardiolipin Antibodies and Thrombosis", Thrombosis Research, 57 (2):247–258 (1990).

Bertina, et al., "Mutation in blood coagulation factor V associated with resistance to activated protein C", Nature, 369:64–67 (1994).

Karges, et al., "Activity of Coaqulation and Fibrinolysis Parameters in Animals", Arzneimittel–Forschung Drug Research, 44 (I), 6,:793–797 (1994).

Bertina et al., "Mutation in Blood Coagulation Factor V Associated with Resistance to Activated Protein C," Nature 369:64–67 (1994).

Karges et al., "Activity of Coagulation and Fibrinolysis Parameters in Animals," Arzneim.–Forsch/Drug Res. 44(1) (6):793–97 (1994).

Kraus et al., "Coagulation Assay with Improved Specificity to Factor V Mutants Insensitive to Activated Protein C," Thrombosis Res. 80(3):255–64 (1994).

*Primary Examiner*—Long V. Le
*Attorney, Agent, or Firm*—Finnegan, Henderson, Farabow, Garrett & Dunner, L.L.P.

[57] ABSTRACT

The invention relates to a plasma which can be used as a calibrator in coagulation tests which detect the degradation of factor V by activated protein C, to the preparation of such a plasma and to its use.

19 Claims, No Drawings

CALIBRATOR FOR USE IN TEST METHODS FOR DETECTING A DEFECTIVE COAGULATION FACTOR V

The invention relates to a plasma which can be used as a calibrator in coagulation tests which detect the degradation of factor V by activated protein C, to the preparation of such a plasma and to its use.

In the first place, the coagulation system in the blood ensures that blood flow is sustained to the tissue which is to be supplied; in the second place, it reacts to injuries by effecting wound closure and thereby ensures that the integrity of the organism is preserved. When coagulation is activated, the active protease thrombin is finally formed by way of a cascade-like system of proteases which activate themselves in a stepwise manner. The formation of thrombin, which is initially very slow, is accelerated by thrombin itself in that the thrombin activates the cofactors factor V and factor VIII by means of proteolytic cleavage. Together with the proteases factor Xa and factor IXa, respectively, these activated cofactors form active enzyme/cofactor complexes on phospholipid surfaces, the activity of which complexes is higher by a factor of approximately 1000 than that of the individual proteases. This positive feedback mechanism gives rise, almost explosively, to the formation of large quantities of thrombin. Thrombin converts fibrinogen into fibrin, normally leading to wound closure and wound healing. In order to prevent a life-threatening spread of the coagulation, which would lead to a closure of the vascular system of the body, that is to thromboses, it is necessary to inhibit the active protease and to prevent the protease being supplied. In the body, active proteases are neutralized by protease inhibitors by means of the formation of covalent complexes. Interruption of the protease supply is initiated by thrombin itself. For this purpose, thrombin binds to the membrane protein thrombomodulin and converts the pro-enzyme protein C into the active protease protein Ca (APC). APC, for its part, forms, together with the cofactor protein S, a complex which proteolytically cleaves, and thereby inactivates, the active cofactors factor VIIIa and factor Va. APC thereby interrupts the powerful stimulating effect produced by these cofactors.

This above-described protein C/protein S system represents an important anticoagulatory mechanism. This is confirmed by the fact that persons with inherited or acquired deficiencies or defects in protein C or protein S are very likely to suffer thromboses, in particular recurring venous thromboses (Esmon, C. T. TCM 2: 214–219, 1992).

Other factors in addition to protein C and protein S are able to exert an influence on the activity of the system. These factors include the von Willebrand factor and factor IXa (Rick, M. E. et al., J. Lab. Clin. Med. 115: 415–421, 1990), which are able to protect factor VIIIa from proteolytic degradation.

Acquired impairments can also be due to the formation of lupus anticoagulants. These are antibodies which are directed against phospholipids and which interfere with the binding, which is necessary for their proper function, of the protease/cofactor complexes to phospholipid surfaces (Amer, L. et al., Thromb. Res. 57: 247–258, 1990).

Finally, a mutant of factor V has very recently been described which can no longer be inactivated, or at least can only be very poorly inactivated, by APC (Bertina, R. M. et al., Nature 369: 64–67, 1994).

These disturbances of the protein C/protein S system, with the exception of protein C itself, can be relatively easily detected diagnostically using a modification of a common screening method (Amer, L. et al., 1990), activated partial thromboplastin time (APTT), which modification is designated APC time (APCT) below. In order to determine the APTT, a plasma sample is brought into contact with an equal volume of a reagent which contains a surface activator, for example silica, kaolin or glass, and phospholipids. This mixture is incubated at +37° C. for a few minutes. During this time, the factors of the coagulation system which are not dependent on calcium (factor XII, factor XI and factor IX) are activated. After adding calcium ions, the remainder of the coagu- lation cascade is activated and thrombin is formed. The resulting quantity of thrombin is then determined either by the conversion of the natural substrate fibrinogen into a clot or by the liberation of a chromophore from a chromogenic substrate. Modifying this APTT into the APCT involves adding activated protein C at the same time as the calcium ions. Since, as described above, APC destroys cofactors VIIIa and Va, there is a resulting deceleration in the formation of thrombin which is dependent on the functional efficiency of the protein C/protein S system.

In coagulation diagnostics, the results are customarily evaluated from a reference curve in terms of percentage of the standard. In this context, a pool of plasmas from healthy blood donors defines the 100% value while the additional calibration points are customarily plotted using dilutions of this plasma pool with physiological sodium chloride solution. However, this approach is not suitable for calibrating the APCT since diluting the plasma prolongs the clotting time (see Example 1); however, in tests for determining the functional efficiency of the protein C/protein S system, the extent to which the clotting time of a pathological sample is prolonged is not as great, owing to the fact that the coagulation activity of the sample is insufficiently suppressed.

In order to carry out a calibration, it is also customary in coagulation diagnostics to mix a normal plasma (100% value) with a plasma from which the factor to be investigated has been removed. This method is also not suitable for calibrating the APCT, as Example 1 demonstrates. As the investigations of Bertina et al., (1994) have shown, a mutation in factor V is an important cause of an APCT which is insufficiently long. A factor V-deficient plasma cannot be used since this plasma is practically incoagulable either in the APTT or the APCT due to the lack of the factor.

In theory, it is also conceivable that the calibrators could be obtained from the blood of affected patients. However, such an approach is not practicable for ethical and technical reasons.

Similar considerations also apply to other impairments of coagulation which are due to mutated coagulation factors.

The underlying object of the invention was, therefore, to find a calibrator which can be prepared independently of blood donations from affected patients.

This object is achieved by providing the embodiments described in the patent claims.

Surprisingly, it has been found that the addition of certain animal plasmas to human plasma leads, in a concentration-dependent manner, to a shortening of the clotting time in an APCT (see Example 2). This finding is all the more surprising since it is known that many animal plasmas have a markedly higher content of factor V than does human plasma (Karges et al., Drug Res. 44: 793–797, 1994). Consequently, it might have been expected that the addition of non-human plasma to a plasma containing mutated factor V would neutralize the shortened APCT since the mutated factor V would be masked by the added factor V. However, precisely the opposite effect was observed (see Example 3). The effect which was found to take place is probably due to the fact that the human activated protein C which was used in the test is not able to cleave non-human coagulation factors proteo- lytically.

Hitherto, it has been well known to the person skilled in the art that animal plasma factor V behaves like human factor V in the known procoagulatory test methods. Consequently, it was to be expected that animal factor V would also behave in a manner corresponding to that of human factor V in the APCT test. Surprisingly, further investigations revealed that the plasmas of the various animal species examined differed in their suitability for use in a calibrator according to the invention. By the provision of the teaching according to the invention, suitability can be determined by means of a simple experiment, with plasmas which are suitable for use in the APCT determination exhibiting a reduction of the clotting time. Plasmas or factor V from the rabbit and the dog have been found to be particularly suitable whereas horse plasma, for example, is less suitable.

The animal factor V preparations may preferably be used in the form of an animal plasma, in the form of enriched or purified factor V fractions or in the form of pure factor V which has been prepared by genetic manipulation. Rabbit and dog plasmas are particularly suitable.

Thus, calibrators which simulate a defect in factor V in functional tests for examining the functional efficiency of factor V and/or of the protein C/protein S system can be prepared by adding such non-human plasmas, or fractions which contain factor V of non-human origin, to a human plasma.

The following examples are intended to illustrate the invention.

| | |
|---|---|
| APCT | activated protein C time |
| APTT | activated, partial thromboplastin time |
| DBA | diethyl barbiturate acetate |
| F.V.-Def. | human plasma having a mutation in factor V |
| SHP | standard human plasma |

EXAMPLE 1

Preparing a calibrator by diluting a pool of plasmas from healthy blood donors

The clotting time was determined using a Schnitger & Gross mechanical coagulometer (from Amelungen). All the reagents were obtained from Behringwerke AG. Standard human plasma was used as the plasma pool from healthy blood donors.

The APTT was determined in accordance with the following protocol: 1 vial of Pathromtino for 5 ml, a phospholipid mixture obtained from human placenta, was dissolved in 5 ml of a suspension of kaolin as the surface activator. The calcium chloride solution (25 mM) was warmed to +370C. before use.

The following were pipetted consecutively into a measuring tube

100 µl of Pathromtino

100 µl of plasma sample.

The mixture was subsequently incubated at +37° C. for 2 minutes, and the clotting time was started by adding 100 µl of calcium chloride solution. At the same time, an inbuilt stopclock was switched on and the time was recorded which elapsed until a clot was detected.

The APCT was determined using the APC sensitivity reagents from Behringwerke. The activator reagent was prepared as for the APTT. The starting reagent, comprising calcium chloride and activated protein C, was dissolved in 5 ml of distilled water and warmed to +37° C. before use.

The following were pipetted consecutively into a measuring tube

100 µl of Pathromtin®

100 µl of plasma sample.

The mixture was subsequently incubated at +37° C for 3 minutes, and the clotting time was started by adding 100 µl of starting reagent. At the same time, an inbuilt stopclock was switched on and the time was recorded which elapsed until a clot was detected.

SHP was diluted to different concentrations using physiological sodium chloride solution or DBA buffer (from Behringwerke), and the APTT and APCT were determined. It can be seen from Table 1 that both the APTT and the APCT increase with increasing dilution of plasma irrespective of the medium employed. Consequently, this method is not suitable for preparing a calibrator which has a shorter APCT than does normal plasma.

TABLE 1

APTT and APCT of a normal, human citrate plasma when diluted with physiological sodium chloride solution or DBA buffer. Values in seconds. NaCl = dilution with physiological sodium chloride solution; DBA = dilution with DBA buffer.

| | | SHP concentration (%) | | | |
|---|---|---|---|---|---|
| Medium | Parameter | 25 | 50 | 75 | 100 |
| NaCl | APTT | 85.0 | 51.5 | 40.6 | 38.3 |
| | APCT | >300 | 233.9 | 153.8 | 142.9 |
| DBA | APTT | 77.9 | 48.3 | 39.0 | ditto |
| | APCT | >300 | 211.9 | 160.6 | |

EXAMPLE 2

Preparing a calibrator by adding non-human plasma to human plasma

The clotting times were determined as described in Example 1.

Table 2 summarizes the clotting times (mean values from duplicate determinations) which were obtained when normal human citrate plasma (SHP) was mixed with rabbit citrate plasma or dog citrate plasma. It can be seen that the APCT of the mixture becomes shorter as the proportion of the non-human plasma increases. The effect of the rabbit plasma is clearly more pronounced than that of the dog plasma. Thus, a defect in the protein C/protein S system can be simulated in the APCT by adding small quantities of non-human plasma to the human plasma. This method is suitable, therefore, for preparing appropriately defined calibrators.

TABLE 2

APCT values obtained when a normal, human citrate plasma is mixed with dog or rabbit citrate plasmas. Values given in seconds.

| | Proportion of the addition in the human plasma (%) | | | | | | |
|---|---|---|---|---|---|---|---|
| Addition | 0 | 4 | 8 | 16 | 33 | 50 | 100 |
| Dog | 145.3 | 100.6 | 76.1 | 49.4 | 34.2 | 27.1 | 21.2 |
| Rabbit | 140.3 | 60.7 | 48 | 39.1 | 30.7 | 26.6 | 25.2 |

EXAMPLE 3

Effect of adding human and non-human plasmas to a human plasma with a defect in the factor V gene The clotting times were determined as described in Example 1.

A normal plasma (SHP; see Example 1) and rabbit citrate plasma were admixed in various concentrations with a human plasma which contained a factor V which APC was only able to inactivate with difficulty, and the effect on the APCT was monitored (Table 3). As expected, an excess of normal, human plasma led to neutralization of the nondegradable factor V so that longer clotting times were observed in the APCT. By contrast, even small additions of rabbit plasma led to an even more pronounced shortening of the APCT, as was also demonstrated in Example 2 using normal human plasma.

TABLE 3

APCT values obtained when mixing a human, factor V-defective plasma with normal human plasma or with rabbit plasma. Values given in seconds. SHP = normal human plasma

| Addition | Portion of the addition in the factor V-defective plasma (%) | | | | | |
|---|---|---|---|---|---|---|
| | 0 | 10 | 25 | 50 | 75 | 100 |
| SHP | 66.3 | 69.8 | 77.5 | 91.1 | 111.2 | 144.0 |
| | 0 | 1 | 2.5 | 5 | | 100 |
| Rabbit | 66.3 | 59.8 | 55.4 | 45.8 | | 44.9 |

I claim:

1. A calibrator for use in test methods for detecting a defective coagulation factor V comprising non-human plasma, or factor V-containing fractions thereof, and human plasma.

2. The calibrator as claimed in claim 1, wherein plasma is used from a species which, in an F.V-dependent or F.Va-dependent test method, gives a different result from that obtained with a normal human plasma.

3. The calibrator as claimed in claim 1, wherein the non-human plasma brings about a reduction of the clotting time, or of an equivalent parameter, in the APC depend assays.

4. The calibrator as claimed in claim 1, wherein citrate plasma or fractions of plasma are preferably used which contain factor V of non-human origin.

5. The calibrator as claimed in claim 1, wherein the human plasma is a human citrate plasma.

6. The calibrator as claimed in claim 1, wherein concentration of the non-human, factor V-containing addition to the human plasma is chosen such that reactivity of said calibrator clearly differs from that without any addition.

7. The calibrator as claimed in claim 6, wherein the addition is chosen such that a clotting time differs by at least 20% from a clotting time obtained with untreated human plasma.

8. A method for preparing a calibrator as claimed in claim 1 for use in coagulation assays, wherein a human plasma is supplemented by adding non-human plasma or factor V-containing fractions from non-human plasma.

9. The calibrator as claimed in claim 1, wherein the non-human plasma is derived from a dog or a rabbit.

10. The calibrator as claimed in claim 5, wherein human citrate plasma is stabilized.

11. The calibrator as claimed in claim 6, wherein the addition to the human plasma is chosen such that a clotting time differs by at least 50% from a clotting time obtained with untreated human plasma.

12. A method of calibration for determining either activated protein C time or activated partial thromboplastin time comprising the steps of:

(1) containing a calibrator as claimed in claim 2 with a reagent which contains a surface activator;

(2) incubating said calibrator and said surface activator;

(3) adding a calcium chloride solution, which contains protein C only for determining said activated protein C time, to said calibrator and (4) measuring said activated protein C time or said activated partial thromboplastin time.

13. The method of calibration as claimed in claim 12, wherein the method examines the functional efficiency of the protein C/protein S system.

14. The method of calibration as claimed in claim 12, wherein said method examines the ability of activated protein C to degrade factor Va.

15. The method of calibration as claimed in claim 12, wherein activated protein C is added exogenously.

16. The method of calibration as claimed in claim 12, wherein the protein C of the sample is activated.

17. The method of calibration as claimed in claim 12, wherein the measurement of activated protein C time or activated partial thromboplastin time is determined by measuring the quantity of thrombin produced by way of the formation of fibrin clot or chromogenically by way of the conversion of a synthetic thrombin substrate.

18. The method as claimed in claim 8, wherein the human plasma contains a mutant factor V which is not a substrate for cleavage by human activated protein C.

19. The calibrator of claim 1, wherein the human plasma contains a mutant factor V which is not a substrate for cleavage by human activated protein C.

* * * * *

UNITED STATES PATENT AND TRADEMARK OFFICE
CERTIFICATE OF CORRECTION

PATENT NO. : 5,753,510
DATED : May 19, 1998
INVENTOR(S) : Michael Kraus

It is certified that error appears in the above-identified patent and that said Letters Patent is hereby corrected as shown below:

Claim 6, Column 5, Line 45, after "wherein", insert --a--;

Claim 12, Column 6, Line 18, "containing" should read --contacting--;

Claim 12, Column 6, Line 23, after "calibrator and", insert --said surface activator; and --.

Signed and Sealed this

Twenty-fourth Day of August, 1999

Attest:

Q. TODD DICKINSON

Attesting Officer

Acting Commissioner of Patents and Trademarks